United States Patent [19]

Schachar

[11] Patent Number: 5,149,712

[45] Date of Patent: Sep. 22, 1992

[54] TREATMENT OF CORNEAL EDEMA WITH DIATRIZOATE SOLUTIONS

[76] Inventor: Ronald A. Schachar, P.O. Box 1039, Denison, Tex. 75020

[21] Appl. No.: 809,129

[22] Filed: Dec. 18, 1991

[51] Int. Cl.$^5$ ............................................. A61K 31/195
[52] U.S. Cl. ...................................... 514/563; 514/912
[58] Field of Search ................................ 514/563, 912

[56] References Cited

PUBLICATIONS

Invest. Radiol (U.S.A.), 1990 25/5 (504–510), See The Embase Abstract 7744096.

Primary Examiner—Frederick E. Waddell
Assistant Examiner—Zohreh A. Fay
Attorney, Agent, or Firm—Vorys, Sater, Seymour & Pease

[57] ABSTRACT

A method for treating corneal edema comprises contacting a cornea that has a reduced light transmissive ability due to edema with an amount of a pharmaceutically acceptable non-toxic salt of diatrizoic acid in an aqueous solution sufficient to improve the light transmissive ability of the cornea.

8 Claims, No Drawings

TREATMENT OF CORNEAL EDEMA WITH DIATRIZOATE SOLUTIONS

BACKGROUND OF THE INVENTION

1. Field of the Invention:

This invention relates to a method for reducing or eliminating corneal opacity due to edema and more particularly to a method for treating corneal edema by topical application of solutions of diatrizoate salts.

2. Brief Description of the Prior Art:

The cornea of the human eye in its normal condition is a thin, curved transparent window that covers the front portion of the globe, provides the major part of the refractive power of the eye and transmits light to the interior of the eye where it is focused on the retina by the crystalline lens. The major structural element of the cornea, occupying most of its thickness, is the stroma, which is a differentiated connective tissue. As such it is composed of collagen fibrils arranged in a regular order at a spacing less than a wavelength of light within a ground mass of glycosaminoclycan (GAG) which serves to support the fibrils and protect them. The stroma typically contains about 75% to 80% by weight of water. This water content is critical for maintaining the transparency of the cornea; if the proportion of water exceeds the normal amount, the cornea becomes edematous and takes on a whitish cloudy appearance, which may become so dense as to obscure vision entirely. Maintaining the proper degree of hydration of the corneal stroma is facilitated by the two layers of cells which bound the stromal layer.

The anterior surface of the cornea is covered with a layer of epithelial cells, which among other functions, prevent the diffusion of water from the tear fluid into the stroma. However, the corneal epithelium itself may under some circumstances become edematous and cloudy.

The posterior surface of the cornea is covered with an endothelial cell layer that both serves as barrier to diffusion of water from the aqueous humor of the anterior chamber into the stroma and actively pumps water out of the stroma to maintain the proper degree of hydration. If either the epithelial layer or the endothelial layer is disrupted or injured so that it cannot perform its function of excluding or removing water from the stroma, a corneal opacity, either localized or general, may develop.

While corneal opacities due to problems in the epithelial or endothelial layer tend to resolve themselves over time as the layers heal, it is sometimes necessary in ophthalmological practice to clear a corneal opacity rapidly. For example, it may be necessary to restore vision while the healing of the relevant layers is occurring. A common occasion in which it is desirable to remove the corneal opacity quickly is when a person having such a condition presents for treatment. Under these conditions, the corneal opacity prevents the ophthalmologist from examining the interior structures of the eye for purposes of diagnosis.

It is known to treat edema of the corneal epithelium or stroma by topical application of glycerin. This method is suitable for treatment of epithelial edema and stromal edema due to breaks in the epithelium, e.g., those caused by abrasion. Perfusion of the anterior chamber with a hypertonic solution of glucose has been shown to reduce the hydration of the corneal stroma. However, a need has continued to exist for additional methods of rapidly clearing corneal opacities due to excessive hydration of the cornea.

SUMMARY OF THE INVENTION

This need has now been met by a method of treating a cornea that has a reduced light transmissive ability due to edema with an amount of a pharmaceutically acceptable non-toxic salt of diatrizoic acid in an aqueous solution sufficient to improve the light transmissive ability of the cornea.

Accordingly, it is an object of the invention to provide a method for treating corneal opacity.

A further object is to provide a method for rapidly restoring transparency to an opaque cornea.

A further object is to provide a method for treating corneal opacity by the use of meglumine diatrizoate.

Further objects of the invention will become apparent from the description of the invention which follows.

DETAILED DESCRIPTION OF THE INVENTION AND PREFERRED EMBODIMENTS

Salts of diatrizoic acid are used as x-ray contrast materials suitable for intravascular injection to assist in visualizing internal structures of the body in radiography. Certain pharmacologically acceptable non-toxic salts of this material are well accepted as intravascular contrast agents and are described in the U.S. Pharmacopeia. Diatrizoic acid is chemically 3,5-diacetamido-2,4,6-triiodobenzoic acid. It is supplied and used principally as either the sodium salt or the salt with meglumine (1-deoxy-1-methylamino-D-glucitol). Either salt may be used alone as an x-ray contrast agent or the salts may be used in combination. Injectable forms of diatrizoate salts comprise solutions of the salts in sterile, pyrogen-free water (water for injection). The diatrizoate salt solutions contain such a concentration of diatrizoate salts as to be hypertonic, i.e., the osmolarity of the solution exceeds the osmolarity of the fluids that are normally in contact with the cornea, i.e., the lacrimal fluid and the aqueous humor. Concentrations of the sodium salt may vary from 20% to 50% by weight of the solution, while solutions of the meglumine salt are supplied in concentrations of 30%, 60%, 70%, 76% and 85% by weight. Because the sodium salt contains more iodine on a weight basis, it is more efficient as an x-ray contrast agent, but tends to be more toxic. The meglumine salt contains less iodine, but its solutions tend to be somewhat viscous. Accordingly, combinations of meglumine diatrizoate and sodium diatrizoate are frequently used in various concentrations and various proportions of the sodium and meglumine salts. For example, solutions of the meglumine and sodium salts of diatrizoic acid are supplied in concentrations of 50/25, 60/30, 52/8, 66/10, 34.3/35, and 28.5/29.1 percent by weight. A preferred solution for the method of this invention is a solution containing 660 milligrams of meglumine diatrizoate and 100 milligrams of sodium diatrizoate per milliliter of solution. Such a solution is sold by E.R. Squibb & Sons as Renografin-76 ®.

The method of the invention is useful for the rapid clearing of corneal opacities, particularly when an ophthalmologist must clarify an opaque cornea in order to examine the interior structures of the eye.

In practicing the invention, a solution of meglumine diatrizoate or sodium diatrizoate or a solution containing both salts in sterile, pyrogen-free water (water for injection) is injected into the anterior chamber of an eye having a corneal opacity. The amount injected will depend to some extent on the degree of corneal opacity present and on the concentration of the aqueous solution of the diatrizoate salt. Typically, about 0.5 milliliter of the solution will be sufficient to effect a rapid clarification of the corneal opacity. The solution of a diatrizoate salt may also be applied topically to the cornea by instillation into the eye. This topical application is especially useful in clearing opacities due to epithelial edema and stromal edema consequent to corneal abrasions.

The invention having now been fully described, it should be understood that it may be embodied in other specific forms or variations without departing form its spirit or essential characteristics. Accordingly, the embodiments described above are to be considered in all respects as illustrative and not restrictive, the scope of the invention being indicated by the appended claims rather than the foregoing description, and all changes which come within the meaning and range of equivalency of the claims are intended to be embraced therein.

I claim:

1. A method for treating corneal edema comprising contacting a cornea that has a reduced light transmissive ability due to edema with an amount of a pharmaceutically acceptable nontoxic salt of diatrizoic acid in an aqueous solution sufficient to improve the light transmissive ability of said cornea.

2. The method of claim 1 wherein said aqueous solution is hypertonic.

3. The method of claim 1 wherein said salt of diatrizoic acid is meglumine diatrizoate.

4. The method of claim 1 wherein said salt of diatrizoic acid is sodium diatrizoate.

5. The method of claim 1 wherein said aqueous solution contains both meglumine diatrizoate and sodium diatrizoate.

6. The method of claim 4 wherein said solution contains about 660 milligrams of meglumine diatrizoate and about 100 milligrams of sodium diatrizoate per milliliter of solution.

7. The method of claim 1 wherein said solution is injected into the anterior chamber of the eye behind said cornea.

8. The method of claim 1 wherein said solution is applied topically to the eye.

* * * * *